United States Patent
Cros et al.

(10) Patent No.: US 11,090,406 B1
(45) Date of Patent: Aug. 17, 2021

(54) ITEM THAT ADHERES TO THE SKIN

(71) Applicant: ELKEM SILICONES FRANCE SAS, Lyons (FR)

(72) Inventors: Gaelle Cros, Ternay (FR); Caroline Moine, Sorbiers (FR); Sebastien Marrot, Lyons (FR)

(73) Assignee: ELKEM SILICONES FRANCE SAS, Lyons (FR)

(*) Notice: Subject to any disclaimer, the term of this patent is extended or adjusted under 35 U.S.C. 154(b) by 534 days.

(21) Appl. No.: 15/763,022

(22) PCT Filed: Sep. 22, 2016

(86) PCT No.: PCT/FR2016/000144
§ 371 (c)(1),
(2) Date: Mar. 23, 2018

(87) PCT Pub. No.: WO2017/051083
PCT Pub. Date: Mar. 30, 2017

(30) Foreign Application Priority Data

Sep. 25, 2015 (FR) .................................. 1501990

(51) Int. Cl.
| C09J 183/04 | (2006.01) |
| A61L 15/58 | (2006.01) |
| A61L 15/22 | (2006.01) |
| A61F 5/443 | (2006.01) |
| A61M 25/02 | (2006.01) |
| A61F 13/02 | (2006.01) |
| C09J 183/06 | (2006.01) |

(52) U.S. Cl.
CPC .............. *A61L 15/58* (2013.01); *A61F 5/443* (2013.01); *A61F 13/0253* (2013.01); *A61F 13/0266* (2013.01); *A61L 15/225* (2013.01); *A61M 25/02* (2013.01); *A61F 13/0283* (2013.01); *A61F 13/0289* (2013.01); *A61M 2025/0266* (2013.01); *C09J 183/04* (2013.01); *C09J 183/06* (2013.01); *Y10T 428/1471* (2015.01); *Y10T 428/2843* (2015.01); *Y10T 428/2848* (2015.01)

(58) Field of Classification Search
None
See application file for complete search history.

(56) References Cited

U.S. PATENT DOCUMENTS

| 2,676,182 A | 4/1954 | Daudt et al. |
| 3,159,601 A | 12/1964 | Ashby |
| 3,159,602 A | 12/1964 | Hamilton |
| 3,220,972 A | 11/1965 | Lamoreaux |
| 3,419,593 A | 12/1968 | Willing |
| 3,508,947 A | 4/1970 | Hughes |
| 3,632,374 A | 1/1972 | Greiller |
| 3,775,452 A | 11/1973 | Karstedt |
| 4,479,987 A | 10/1984 | Koepke et al. |
| 4,830,887 A | 5/1989 | Reiter |
| 4,838,253 A * | 6/1989 | Brassington ............ A61L 15/26 602/48 |
| 4,933,215 A | 6/1990 | Naruse et al. |
| 4,974,533 A | 12/1990 | Ishizuka et al. |
| 5,145,933 A * | 9/1992 | Grisoni ............... A61L 26/0019 528/15 |
| 8,586,191 B2 * | 11/2013 | Lorentz ................... C08L 83/04 428/447 |
| 10,662,330 B2 * | 5/2020 | Auzias ................... C09J 183/04 |
| 10,702,625 B2 * | 7/2020 | Moine ................. A61F 13/0246 |
| 10,758,640 B2 * | 9/2020 | Moine .................... A61L 15/585 |
| 2007/0004359 A1 * | 1/2007 | Srinivasan ........... H03G 3/3068 455/232.1 |
| 2007/0202245 A1 * | 8/2007 | Gantner .................. A61L 15/58 427/2.1 |
| 2012/0328787 A1 * | 12/2012 | Marrot ................. C09D 183/04 427/387 |
| 2013/0053749 A1 * | 2/2013 | Lorentz ................... C08L 83/00 602/54 |
| 2014/0004359 A1 * | 1/2014 | Marrot .................... C08L 83/04 428/447 |
| 2018/0177911 A1 | 6/2018 | Moine et al. |

FOREIGN PATENT DOCUMENTS

| EP | 0057459 | 8/1982 |
| EP | 0188978 | 7/1986 |
| EP | 0190530 | 8/1986 |
| EP | 0300620 | 1/1989 |
| EP | 0537086 | 4/1993 |
| EP | 0633757 | 1/1995 |
| EP | 0633758 | 1/1995 |
| EP | 0737721 | 10/1996 |
| EP | 2001424 | 12/2008 |
| FR | 2971971 | 8/2012 |
| FR | 3004990 | 10/2014 |
| FR | 3037800 | 12/2016 |
| WO | 93/19709 | 10/1993 |

(Continued)

OTHER PUBLICATIONS

International Search Report dated Nov. 24, 2016, and English Translation of the International Search Report corresponding to International Patent Application No. PCT/FR2016/000144, 5 pages.
Written Opinion of the international Searching Authority dated Nov. 24, 2016, corresponding to International Patent Application No. PCT/FR2016/000144, 5 pages.
"Soft Skin Adhesive Gel for Scar Care and Wound Management HC2 2022 A&B Technical Data Sheet n° SIL 15 037 3. Mar. 2015", XP055268817, Retrieved from the Internet: URL:http://www.silbione.com/wp-content/uploads/2014/01/Silbione HC2 2022 AB SIL150373.pdf [retrieved on Apr. 26, 2016] the whole document, 3 pages.

*Primary Examiner* — Anish P Desai
(74) *Attorney, Agent, or Firm* — Dentons US LLP

(57) ABSTRACT

Items that adhere to the skin for medical or paramedical use and methods of making and using the same are described.

49 Claims, No Drawings

(56) References Cited

FOREIGN PATENT DOCUMENTS

| WO | 93/19710 | 10/1993 | | |
|---|---|---|---|---|
| WO | 2007/113597 | 10/2008 | | |
| WO | 2011/092404 | 8/2011 | | |
| WO | 2011/092404 A1 | 8/2011 | | |
| WO | WO-2017129429 A1 * | 8/2017 | ............... | C08K 5/56 |

* cited by examiner

ITEM THAT ADHERES TO THE SKIN

CROSS-REFERENCE TO PRIOR APPLICATIONS

This application is a National Stage of PCT/FR2016/000144, filed Sep. 22, 2016, and designating the United States (published on Mar. 30, 2017, as WO 2017/051083 A1), which claims priority under 35 U.S.C. § 119 to French Application No. 1501990, filed Sep. 25, 2015, each hereby expressly incorporated by reference in its entirety and each assigned to the assignee hereof.

The present invention relates to an adhesive item that is useful for use against the skin and more particularly as:
- a dressing that adheres to the skin, or part of such a dressing, in particular intended for non-traumatic removal from healthy skin and from a wound, or
- a device for holding in place medical accessories, or part of such a device, used in contact with the skin, of sensor, probe, catheter or needle type.

The use of silicone gels in medical devices intended to be in contact with the skin is currently very widespread. This is because the intrinsic properties of silicone gels mean that they adhere rapidly to dry skin, but do not stick to the surface of a moist wound, consequently not causing any damage when they are removed. Silicone gels also have the advantage of being able to be assembled to a large number of supports while at the same time being inert with respect to the organism, thus avoiding any problem of toxicity when they are used in human beings. Silicone gels are, inter alia, used for the treatment of wounds or scars because they provide the medical device with properties that facilitate recovery of the patient while maintaining a moist environment around the wound and thus make it possible to maintain the hydration of the damaged tissues. These properties are well documented and include the fact that silicone gels do not leave particles or fibers in the wound, are flexible on the skin and are comfortable.

Thus, many medical devices integrate silicone gels as adhesive to the skin or as contact layer in contact with a wound to be treated.

The prior art describes various types of medical devices comprising these silicone gels.

For example, patent EP-A-0633758 from the company Moelnlycke AB describes a dressing comprising a layer of hydrophobic silicone gel, a layer of support material and an absorbent substance placed on the side of the support, in which the support material and the layer of gel comprise penetrating perforations which mutually coincide at least in the region of the absorbent substance.

Patent EP-A-0633757 from the company Moelnlycke AB describes the process for producing such a dressing, which process involves a pre-step which consists in blowing cold air over the bottom face of the perforated support material covered with a liquid mixture of precursor silicone for the silicone gel, so that the perforations of the support material are not blocked. The stream of cold air guarantees that the liquid mixture of precursor silicone for the silicone gel does not begin to harden before having the time to spread over the support material. The stream of cold air passing through the support material also prevents the liquid mixture of precursor silicone for the silicone gel from spreading into the perforations of said material. The silicone gel is then formed by a crosslinking reaction under the action of heat.

Patent EP-A-2001424 from the company Brightwake Ltd describes a removable adhesive laminate comprising a structural layer comprising, on at least one part of one side thereof, a hydrophobic silicone gel and comprising, on at least one part of the other side thereof, a pressure-sensitive adhesive. The presence of the pressure-sensitive adhesive facilitates the assembly of the composite dressings which comprise this type of laminate. The presence of the pressure-sensitive adhesive makes it possible to attach secondary components of the dressing, for example absorbent materials, to the laminate, and also fluid-impermeable barrier layers in order to prevent a fluid, such as the exudate from the wound, from escaping from the dressing.

Patent EP-A-0300620 from the company Dow Corning SA describes a surgical dressing, particularly suitable for treating burns, comprising a film formed from a silicone gel which comprises a surface which faces the wound and is laminated on the other surface with a film of silicone elastomer.

As examples of dressings sold on the market using silicone gels, mention may be made of:
- the dressings sold under the brand name Mepitel®, which are silicone-gel-coated polyamide knitted dressings intended to be in contact with the skin;
- the dressings sold under the brand names Allevyn® Life, Allevyn® Life Sacrum, Mepilex® Border and Allevyn® Life Heel, which use a compress of composite hydrocellular foam placed between a silicone-gel-based microperforated adhesive interface, in contact with the wound, and a highly permeable waterproof external film;
- the dressings sold under the brand name Cica-Care®;
- the dressings sold under the brand name Urgotul®;
- the dressings sold under the brand name Cerederm®.

Silicone gels are also widely used in devices for holding in place medical items used in contact with the skin, of sensor, probe, catheter or needle type. Examples are illustrated in patent applications FR-A1-2971971 and FR-A1-3004990 by the company Zodiac Automotive Division. As an example of a commercial product, mention may be made of Mepitel® Film.

However, silicone gels remain fragile when they are subjected to shear stresses, for example following repeated rubbing of an item of clothing on a dressing applied to the skin of a patient or when they are used as adhesives in devices for attaching ostomy bags. Thus, the various stresses undergone by the gel degrade it and lead to the appearance of gel traces in the periphery of the medical device. Measurement of the static shear strength makes it possible to quantify the strength of a silicone gel subjected to shear stresses. The static shear strength is thus defined as the time required for an area of standard contact of an adhesive silicone gel to separate from a standard flat surface when it is subjected to a standard weight, by sliding in a direction parallel to this surface when it is applied. This measurement gives an indication of the capacity of the adhesive silicone gel to withstand static forces in the plane and is determined according to the method described in the document "FINAT Test Method no. 8" (FINAT Technical Handbook 6th edition, 2001). In the present statement, the test is carried out with test specimens (support coated with a gel) having a size of 25 mm×45 mm and on a plate of stainless steel type. This test thus makes it possible to also evaluate the cohesive power or the cohesiveness of an adhesive silicone gel. The lower the cohesiveness of the silicone gel, the more it degrades when it is subjected to static shear stresses, which results in the appearance of traces of gel on the periphery of the medical device. The medical device industry, in particular with respect to those devices using silicone gels that adhere to the skin, is always awaiting silicone gels which have an improved static shear strength.

However, the improvement in the cohesiveness of silicone gels must not be to the detriment of the capacity of said gel to adhere to the skin. Indeed, it is important for silicone gels to adhere well to the skin because they are also used as a means for attaching the item to the user's skin and for holding it in place in numerous medical devices.

The skin-adhesion force of a silicone gel is evaluated by means of the following two properties:
- the tack which evaluates how well a silicone gel rapidly adheres to the skin, and
- the adhesive power or peel capacity at an angle of 180° which evaluates the force required to detach a silicone gel from a surface of a material simulating the behavior of skin (sheet of Bristol paper).

A method termed "Probe Tack" method is known for assessing and evaluating the tack, and is described in the standard ASTM D2979. This test makes it possible to measure the tack of the adhesive. The principle is the following for the silicone gels described in the present statement: a cylindrical punch with a flat face is brought into contact with the adhesive film which is deposited on the substrate. The punch is then kept in contact with the adhesive for a contact time of 1 second at a constant pressure of 100 gf/cm². Next, the punch is detached from the film at a constant speed of 10 mm/s, and the force required to separate the adhesive from the rod is measured and expressed in gf/cm² (the detachment energy is expressed in mJ/cm²). A silicone gel which has a tack of greater than 600 gf/cm² measured according to the conditions described above is a silicone gel that is particularly desired and suitable for use in medical devices in contact with the skin.

The adhesive power or peel capacity of a silicone gel with respect to the skin is the force required to detach it from a sheet of Bristol paper, simulating the skin, of well-defined size, at an angle of 180° and at a constant speed of 300 mm/min and with the aid of a 10 N (Newtons) force cell in the case of silicone gels. It is evaluated by the method described in the document FINAT Test Method n° 1 (FINAT Technical Handbook 6th edition, 2001). Thus, an item that adheres to the skin which has defined dimensions (in the present statement of 40 mm×150 mm) and which comprises a support onto which a layer of silicone gel is coated is applied by bringing the silicone gel into contact with a sheet of Bristol paper. The item is then detached and the force is measured and related to the width of the item and expressed in N/cm.

Thus, the object of the present invention is to provide novel items that adhere to the skin, comprising a support onto which is coated an adhesive silicone gel having an improved static shear strength so as to allow prolonged use in medical devices subjected to stresses of this type, for example following repeated rubbing by an item of clothing on a dressing applied to the skin of a patient, or high tensions, for instance when they are used as adhesives in devices for attaching ostomy bags.

Another object of the present invention is to provide novel items that adhere to the skin, comprising an adhesive silicone gel having good adhesion properties.

These objectives are achieved by the invention which relates to an item that adheres to the skin, comprising:
- a support S having a top face S1 and a bottom face S2,
- optionally at least one tie primer C1 applied on at least one part or on all of the top face S1 of said support S,
- at least one layer D1 applied continuously or discontinuously on the top face S1 of said support S or on said tie primer C1 when it is present, and which consists of a silicone gel E that adheres to the skin, having the following properties:
  a) a penetrability of between 80 mm/10 and 300 mm/10, preferably of between 80 mm/10 and 200 mm/10, measured according to the standard NF ISO 2137 with a penetrometer having a rod and a cone and the sum of the weights of which is equal to 62.5 g, and
  b) a tack of between 600 gf/cm² and 900 gf/cm², preferably between 700 gf/cm² and 850 gf/cm² for a layer of 200 g/m² coated onto a PET support having a thickness of 36 μm and measured according to the standard ASTM D2979,
  c) an adhesive power of between 1.05 N/cm and 1.25 N/cm, preferably of between 1.10 N/cm and 1.20 N/cm, for a layer of 200 g/m² coated onto a PET support having a thickness of 36 μm and measured according to the FINAT no. 1 test method by bringing into contact with a strip of Bristol paper into contact with a peel angle of 180°, and
  d) a static shear strength at 23° C. greater than 3 hours measured according to the FINAT no. 8 test method for a layer of 200 g/m² coated onto a PET support having a thickness of 36 μm; and
- optionally at least one protective layer F consisting of a peel-off protective material and applied on said layer D1, said silicone gel E being obtained by crosslinking of a silicone composition X comprising:
1) at least one organopolysiloxane A comprising, per molecule, at least two $C_2$-$C_6$ alkenyl radicals each bonded to a silicon atom and consisting:
  (i) of at least two units of formula (A1):

$$(Y)_a(Z)_b SiO_{(4-(a+b))/2} \quad (A1)$$

in which:
  Y represents a $C_2$ to $C_6$ akenyl group, and preferably a vinyl group,
  Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl or cyclooctyl groups, and aryl groups such as xylyl, tolyl and phenyl groups;
  a and b represent integers, a being 1, 2 or 3, b being 0, 1 or 2 and (a+b) being 2 or 3;
  (ii) and optionally of at least one unit of formula (A2):

$$(Z)_c SiO_{(4-c)/2} \quad (A2)$$

in which:
  Z has the same meaning as above, and
  c represents an integer which is 2 or 3.

2) at least one organopolysiloxane B comprising, per molecule, at least two hydrogen atoms each bonded to a silicon atom, and preferably at least three hydrogen atoms each bonded to a silicon atom,
3) at least one hydrosilylation catalyst C,
4) at least one hydrosilylation reaction inhibitor D,
5) optionally at least one additive K, and
6) between 1.5% and 3.5% by weight, and preferably between 1.75% and 3.0% by weight, relative to the total weight of the silicone composition X, of at least one silicone resin Z having alkenyl groups bonded to silicon atoms and comprising:

a) at least one siloxyl unit of formula (I):

$$YR_aSiO_{\frac{(3-a)}{2}} \quad (I)$$

in which:
  Y represents a $C_2$ to $C_6$ akenyl group, and preferably a vinyl group,
  R is a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl or cyclooctyl groups, and aryl groups such as xylyl, tolyl and phenyl groups, and
  a=0, 1 or 2, and preferably a=1 or 2
b) at least one siloxy unit of formula (II):

$$R_bSiO_{\frac{(4-b)}{2}} \quad (II)$$

in which R has the same definition as above and b=1, 2 or 3; and
c) at least one siloxy unit Q of formula (III):

$$SiO_{\frac{4}{2}} \quad (III)$$

with the following conditions:
a) the amounts by weight of the organopolysiloxanes A, B and Z are determined such that the value of the ratio $RH_{alk}=n_H/t_{Alk}$ is included in the following range: $0.10 \leq RH_{alk} \leq 0.80$, preferably in the following range $0.20 \leq RH_{alk} \leq 0.80$, and even more preferentially in the following range $0.20 \leq RH_{alk} \leq 0.75$, with $n_H$=number of moles of hydrogen atom directly bonded to a silicon atom of the organopolysiloxane B and $t_{Alk}$=number of moles of alkenyl directly bonded to a silicon atom of the organopolysiloxane A and of the silicone resin Z, and
b) the viscosities and the amounts by weight of the constituents of the silicone composition X are chosen such that the viscosity of the silicone composition X is between 200 mPa·s and 100 000 mPa·s at 25° C., and preferably between 200 mPa·s and 80 000 mPa·s at 25° C.

The applicant has implemented considerable research means and numerous experiments to achieve this objective among others. At the end of this, it found, to its credit, entirely surprisingly and unexpectedly, that adding to a silicone composition, which is a precursor of a silicone gel via a polyaddition reaction, an amount by weight, chosen from a specific range, of a silicone resin having siloxy units Q of formula (III) and alkenyl groups bonded to silicon atoms, makes it possible not only to very much improve the static shear strength of the silicone gel obtained, but also to improve its ability to adhere to the skin.

The improvement in the shear strength, that can reach a factor of 10, and in the ability to adhere to the skin, of the silicone gels according to the invention, allows an effective and prolonged use in medical devices subject to static shear stresses, for example following repeated rubbing by an item of clothing on a dressing applied to the skin of a patient, or when they are used as adhesives in devices for attaching ostomy bags. It therefore has the advantage of not leaving residues on the skin, even when it is used in medical devices that undergo considerable static shear stresses.

For the purposes of the present invention, the expression "silicone gel" denotes a crosslinked silicone product characterized in particular by a degree of penetration (or "penetratability") of between 50 and 500 tenths of one mm. It is measured by penetrometry according to the standard NF ISO 2137, using a Petrotest penetrometer, model PNR 12, with a total weight of the rod and cone fixed at 62.5 g. The cone penetrability of a silicone gel is determined at 25° C. by measuring the depth of penetration of the cone into the sample, said depth being obtained by releasing the cone assembly of the penetrometer and leaving the cone to act for 5 seconds.

The silicone gels according to the invention themselves have a degree of penetration of between 80 mm/10 and 300 mm/10, and preferably of between 80 mm/10 and 200 mm/10.

All the viscosities under consideration in the present description correspond to a "Newtonian" dynamic viscosity magnitude at 25° C., i.e. the dynamic viscosity which is measured, in a manner that is known per se, with a Brookfield viscometer at a shear rate gradient that is low enough for the measured viscosity to be independent of the rate gradient.

According to one preferred embodiment, the invention relates to an item that adheres to the skin, comprising:
  a support S having a top face S1 and a bottom face S2,
  at least one tie primer C1 applied on at least one part or on all of the top face S1 of said support S,
  at least one layer D1 applied continuously or discontinuously on said tie primer C1, and which consists of a silicone gel E that adheres to the skin, having the following properties:
    a) a penetrability of between 80 mm/10 and 300 mm/10, preferably of between 80 mm/10 and 200 mm/10, measured according to the standard NF ISO 2137 with a penetrometer having a rod and a cone and the sum of the weights of which is equal to 62.5 g, and
    b) a tack of between 600 gf/cm² and 900 gf/cm², preferably between 700 gf/cm² and 850 gf/cm² for a layer of 200 g/m² coated onto a PET support having a thickness of 36 μm and measured according to the standard ASTM D2979,
    c) an adhesive power of between 1.05 N/cm and 1.25 N/cm, preferably of between 1.10 N/cm and 1.20 N/cm, for a layer of 200 g/m² coated onto a PET support having a thickness of 36 μm and measured according to the FINAT no. 1 test method by bringing a strip of Bristol paper into contact therewith with a peel angle of 180°, and
    d) a static shear strength at 23° C. greater than 3 hours measured according to the FINAT no. 8 test method for a layer of 200 g/m² coated onto a PET support having a thickness of 36 μm; and
  optionally at least one protective layer F consisting of a peel-off protective material and applied on said layer D1,
  said silicone gel E being obtained by crosslinking of a silicone composition X comprising:
    1) at least one organopolysiloxane A comprising, per molecule, at least two $C_2$-$C_6$ alkenyl radicals each bonded to a silicon atom and consisting:

(i) of at least two siloxy units of formula (A1):

$$(Y)_a(Z)_b SiO_{(4-(a+b))/2} \quad (A1)$$

in which:
Y represents a $C_2$ to $C_6$ akenyl group, and preferably a vinyl group,
Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl or cyclooctyl groups, and aryl groups such as xylyl, tolyl and phenyl groups;
a and b represent integers, a being 1, 2 or 3, b being 0, 1 or 2 and (a+b) being 2 or 3;
(ii) and optionally of at least one siloxy unit of formula (A2):

$$(Z)_c SiO_{(4-c)/2} \quad (A2)$$

in which:
Z has the same meaning as above, and
c represents an integer which is 2 or 3.
  2) at least one organopolysiloxane B comprising, per molecule, at least two hydrogen atoms each bonded to a silicon atom, and preferably at least three hydrogen atoms each bonded to a silicon atom,
  3) at least one hydrosilylation catalyst C,
  4) at least one hydrosilylation reaction inhibitor D,
  5) optionally at least one additive K, and
  6) between 1.5% and 3.5% by weight, and preferably between 1.75% and 3.0% by weight, relative to the total weight of the silicone composition X, of at least one silicone resin Z having alkenyl groups bonded to silicon atoms and comprising:
    a) at least one siloxy unit of formula (I):

$$YR_a SiO_{\frac{(3-a)}{2}} \quad (I)$$

in which:
      Y represents a $C_2$ to $C_6$ akenyl group, and preferably a vinyl group,
      R is a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl or cyclooctyl groups, and aryl groups such as xylyl, tolyl and phenyl groups, and
      a=0, 1 or 2, and preferably a=1 or 2
    b) at least one siloxy unit of formula (II):

$$R_b SiO_{\frac{(4-b)}{2}} \quad (II)$$

in which R has the same definition as above and b=1, 2 or 3; and
    c) at least one siloxy unit Q of formula (III):

$$SiO_{\frac{4}{2}} \quad (III)$$

with the following conditions:
    a) the amounts by weight of the organopolysiloxanes A, B and Z are determined such that the value of the ratio $RH_{alk}=n_H/t_{Alk}$ is included in the following range: $0.10 \leq RH_{alk} \leq 0.80$, preferably in the following range $0.20 \leq RH_{alk} \leq 0.80$, and even more preferentially in the following range $0.20 \leq RH_{alk} \leq 0.75$, with $n_H$=number of moles of hydrogen atom directly bonded to a silicon atom of the organopolysiloxane B and $t_{Alk}$=number of moles of alkenyl directly bonded to a silicon atom of the organopolysiloxane A and of the silicone resin Z, and
    b) the viscosities and the amounts by weight of the constituents of the silicone composition X are chosen such that the dynamic viscosity at 25° C. of the silicone composition X is between 200 mPa·s and 100 000 mPa·s, and preferably between 200 mPa·s and 80 000 mPa·s.

According to one preferred embodiment, the support S is a woven, nonwoven or knitted textile, or a plastic film.

The term "nonwoven" is intended to mean any structure consisting of textile materials, such as fibers, continuous filaments or cut yarns, regardless of the nature or origin thereof, formed into a net by any means, and linked by any means, excluding intertwining of yarns.

Nonwoven textiles are products that have the appearance of porous textiles composed mainly of fibers and are produced by processes other than spinning, weaving, knitting or knotting.

A large variety of plastics may be suitable for use as support S according to the invention. Examples comprise: polyvinyl chloride, polypropylene, regenerated cellulose, polyethylene terephthalate (PET) and polyurethane, in particular blown molten polyurethane.

Preferably, the support S is a perforated flexible polyurethane film or a continuous flexible polyurethane film. This flexible polyurethane film can be produced from blown molten polyurethane.

Preferentially, a transparent or translucent flexible polyurethane film is used. When the adhesive item has a use as a dressing, the use of a transparent or translucent film has the advantage of making it possible to observe the wound, the injury or the site of entry of a catheter on which the dressing must be centered.

Preferably, said support S is a flexible polyurethane film having a thickness of from 5 to 600 μm, preferably from 5 to 250 μm and even more preferentially from 10 to 100 μm.

As an example of a flexible polyurethane film, mention may be made of those which are used in the dressings sold by the company Smith & Nephew under the brand name Opsite®, or by the company 3M under the brand name Tegaderm® or else by Laboratoires URGO under the brand name Optiskin®. These dressings consist of a transparent adhesive thin polyurethane film (of about 20 to 50 μm). Their transparency allows visual verification of the area to be treated.

As another example of a flexible polyurethane film, mention may also be made of those sold under the brand names Platilon® by the company Bayer Material Science and Inspire® by the company Coveris Advanced Coatings.

According to one preferred embodiment, the support S is a continuous flexible film which is permeable to air and impermeable to fluids.

The film may have a moisture vapor transmission rate (MVTR) which is variable according to the intended application. A technique for measuring the moisture vapor transmission rate in liquid contact is described in the standard NF-EN 13726-2. Preferably, the flexible polyurethane film will be chosen so as to obtain a dressing having a moisture vapor transmission rate of greater than 300 g/m²/24 hours, preferably greater than or equal to 600 g/m²/24 hours, more preferably greater than or equal to 1000 g/m²/24 hours.

According to another particular embodiment, the invention relates to an item that adheres to the skin, characterized in that the support S is a flexible polyurethane film and comprises, on at least one part of the bottom face S2, a pressure-sensitive adhesive.

According to one advantageous variant of the invention, the continuous flexible polyurethane film is perforated so as to be able to promote exudate circulation.

Thus, the adhesive item according to the invention is, according to one particular embodiment, a removable adhesive laminate and has the advantage of being able to be used as a contact layer in contact with the skin in various types of medical devices, such as dressings for example.

The pressure-sensitive adhesive can be any of the numerous pressure-sensitive adhesives known from the art. These adhesives, generally in an anhydrous and solvent-free form, are permanently adhesive at ambient temperature and adhere firmly to a variety of dissimilar surfaces during simple contact, without the need to use more than the pressure of a finger or the hand. They do not require activation by water, solvent or heat in order to have a strong maintaining adhesive force. Examples of pressure-sensitive adhesives comprise rubber/resin adhesives, which are mixtures of rubber material and of hard resin, and acrylic (or acrylate) adhesives. The class of pressure-sensitive adhesives that is currently preferred for use in the present invention is that of the acrylic adhesives.

According to one particular embodiment, the support S is a perforated flexible polyurethane film or a continuous flexible polyurethane film having a top face S1 and a bottom face S2 and which is impermeable to air and to fluids in its parts included between the perforations.

In this particular embodiment, it is advantageous for the perforations of the support S to be circular and have a diameter of 50 μm to 10 mm.

As examples of tie primers C1 or adhesion primers, mention may be made of:
- primers formulated in a solvent medium. An example is described in patent application WO 2011/092404 by the company Bluestar Silicones France, wherein a primer consists of an active material (organopolysiloxane oil comprising a hydrosilyl function (SiH) and Si-alkenyl or a silicone resin having hydrosilyl functions) diluted in a silicone solvent (cyclopentasiloxane);
- the primers described in the French patent application filed under no. FR 15 01350 in the name of the company Bluestar Silicones, and
- silicone elastomer primers which are prepared from precursor compositions which crosslink via a hydrosilylation reaction comprising adhesion promoters which are usually silanes that make it possible to improve the adhesion on various substrates (polyamide, polyester or polyurethane substrates).

The protective layer F consisting of a peel-off protective material can consist of one or more parts which can be peeled off before use. This protective layer preferably covers the entire surface of the gel of the adhesive item and may be made of any material commonly used as protection by those skilled in the art in the dressings field. It may for example be in the form of a film, for example a polyolefin film, such as polyethylene or polypropylene, or a polyester film. This film may advantageously be treated on at least one of its faces with a silicone compound such as a silane, a fluoro compound, or a silicone and fluoro compound. The choice of the material is in general adjusted to the nature of the silicone gel. The protective layer F consisting of a peel-off protective material preferably has a thickness of between 10 and 100 μm, for example of about 50 μm.

According to another particular embodiment, the item that adheres to the skin according to the invention is characterized in that it comprises one or more layers N comprising an absorbent substance 0, optionally separated by one or more intermediate layers P, placed on the support S on the side of the bottom face S2 of the support S.

Preferably, the absorbent substance 0 is chosen from the group consisting of: a hydrophilic foam, a fabric pad, a hydrogel, a hydrocolloid and an alginate. Preferably, the absorbent substance 0 is a polyurethane foam.

Preferably, the amounts of silicone gel E according to the invention are determined so as to obtain coatings having a silicone gel content of between 20 and 500 g/m² of support, preferably between 40 and 250 g/m² and even more preferentially between 80 and 350 g/m².

As technique for depositing the composition X according to the invention, mention may for example be made of the coating techniques carried out using a knife, in particular a knife-over-roll, a floating knife or a knife-over-blanket, or by padding, that is to say by squeezing between two rolls, or else by lick roll, rotary machine, reverse roll, transfer, or spraying.

As other coating technique, mention may be made of the curtain coating technique. Curtain coating is a process for applying a coating liquid to an item or a support. Curtain coating is characterized by the formation of a freely falling curtain of a coating liquid which falls from the lip of the hopper and, under gravity, encounters the item moving through the curtain so as to form a coat (or a coating). This technique has been widely used in the field of the preparation of multilayer photosensitive silver supports (see for example U.S. Pat. No. 3,508,947 or EP537086).

It is known that the quality of the coating depends on the quality of the freely falling curtain. It is preferable for the curtain to have a stable laminar flow from the place where it forms to the line of encounter with the moving support. If this is not the case, the surface tension will lead the curtain to contract toward the interior and to interrupt the laminar flow. In order to prevent this problem, it is known practice to use edge guides to seize the freely falling curtain at its edges and to prevent it from contracting toward the interior owing to the surface tension. Examples of such systems are described in U.S. Pat. Nos. 4,933,215, 4,479,987, 4,974,533, 3,632,374, 4,479,987, EP537086 and U.S. Pat. No. 4,830,887.

According to the invention, the organopolysiloxane A comprises, per molecule, at least two $C_2$-$C_6$ alkenyl radicals each bonded to a silicon atom and consists:
(i) of at least two units of formula (A1):

in which:
Y represents a monovalent radical containing from 2 to 6 carbon atoms, having at least one alkenyl group,
Z represents a monovalent radical containing from 1 to 20 carbon atoms and not comprising an alkenyl group,
a and b represent integers, a being 1, 2 or 3, b being 0, 1 or 2 and (a+b) being 2 or 3;
(ii) and optionally of at least one unit of formula (A2):

in which:

Z has the same meaning as above, and c represents an integer which is 2 or 3.

It is understood in formula (A1) and in formula (A2) above, that, if several radicals Y and Z are present, they may be identical to or different than one another.

In formula (A1), the symbol a can preferentially be 1 or 2, more preferentially 1. Furthermore, in formula (A1) and in formula (A2), Z may preferentially represent a monovalent radical chosen from the group formed by an alkyl group containing 1 to 8 carbon atoms, optionally substituted with at least one halogen atom, and an aryl group. Z may advantageously represent a monovalent radical chosen from the group formed by methyl, ethyl, propyl, 3,3,3-trifluoropropyl, xylyl, tolyl and phenyl. In addition, in formula (A1), Y may advantageously represent a radical chosen from the group consisting of vinyl, propenyl, 3-butenyl and 5-hexenyl. Preferably, the symbol Y is a vinyl and the symbol Z is a methyl.

When it is a question of linear organopolysiloxanes, the organopolysiloxane A essentially consists:
of siloxyl units "D" chosen from the units of formulae $(Y)_2SiO_{2/2}$, $(Y)(Z)SiO_{2/2}$ and $(Z)_2SiO_{2/2}$;
and of siloxyl units "M" chosen from the units of formulae $(Y)_3SiO_{1/2}$, $(Y)_2(Z)SiO_{1/2}$, $(Y)(Z)_2SiO_{1/2}$ and $(Z)_3SiO_{2/2}$
with the condition that at least two siloxy units which comprise a group Y are present in the chemical structure of the organopolysiloxane A,
and the symbols Y and Z are as defined above.

By way of example of units "D", mention may be made of dimethylsiloxy, methylphenylsiloxy, methylvinylsiloxy, methylbutenylsiloxy, methylhexenylsiloxy, methyldecenylsiloxy and methyldecadienylsiloxy groups.

By way of example of units "M", mention may be made of trimethylsiloxy, dimethylphenylsiloxy, dimethylvinylsiloxy and dimethylhexenylsiloxy groups.

These organopolysiloxanes, in particular when they are linear, can be oils having a dynamic viscosity at 25° C. of between 50 mPa·s and 120 000 mPa·s, preferentially between 100 mPa·s and 80 000 mPa·s.

When the organopolysiloxane is a cyclic organopolysiloxane, it can consist of siloxyl units "D" chosen from the units of formulae $Y_2SiO_{2/2}$, $YZSiO_{2/2}$ and $Z_2SiO_{2/2}$, with the condition that at least two siloxy units comprising a group Y are present in the chemical structure of the organopolysiloxane A. Examples of such units "D" are described above. This cyclic polyorganosiloxane can have a dynamic viscosity at 25° C. of between 1 mPa·s and 5 000 mPa·s.

Examples of organopolysiloxane A are:
polydimethylsiloxanes comprising dimethylvinylsilyl end groups;
poly(methylphenylsiloxane-co-dimethylsiloxane)s comprising dimethylvinylsilyl end groups;
poly(vinylmethylsiloxane-co-dimethylsiloxane)s comprising dimethylvinylsilyl end groups;
poly(dimethylsiloxane-co-vinylmethylsiloxane)s comprising trimethylsilyl end groups; and
cyclic polymethylvinylsiloxanes.

The organopolysiloxanes A which are polydimethylsiloxanes comprising dimethylvinylsilyl end groups having a dynamic viscosity at 25° C. of between 50 mPa·s and 120 000 mPa·s, and preferably of between 100 mPa·s and 80 000 mPa·s, are particularly advantageous. The formula of this type of particularly advantageous organopolysiloxane A is $M^{Vi}D_xM^{Vi}$, in which formula:

$M^{Vi}$=siloxy unit of formula: $(vinyl)(CH_3)_2SiO_{1/2}$

D=siloxyl unit of formula: $(CH_3)_2SiO_{2/2}$, and x is a number between 0 and 1000, and preferably between 5 and 1000.

The organopolysiloxane B according to the invention bears at least two hydrogen atoms bonded to silicon atoms, and preferably at least three hydrogen atoms bonded to silicon atoms. According to one preferred embodiment, this organopolysiloxane B comprises:
(i) at least two units of formula (B1), and preferably at least three units of formula (B1):

$$(H)_d(L)_eSiO_{(4-(d+e))/2} \qquad (B1)$$

in which:

L represents a monovalent radical other than a hydrogen atom,

H represents a hydrogen atom, d and e represent integers, d being 1 or 2, e being 0, 1 or 2 and (d+e) being 1, 2 or 3; and preferably the sum (d+e) is equal to 2 or 3, and optionally other units of formula (B2):

$$(L)_fSiO_{(4-f)/2} \qquad (B2)$$

in which:

L has the same meaning as above, and f represents an integer which is 0, 1, 2 or 3, and preferably f is equal to 2 or 3.

It is understood in formula (B1) and in formula (B2) above that, if several groups L are present, they may be identical to or different than one another. In formula (B1), the symbol d may preferentially be equal to 1. Furthermore, in formula (B1) and in formula (B2), L may preferably represent a monovalent radical chosen from the group formed by an alkyl group containing 1 to 8 carbon atoms, optionally substituted with at least one halogen atom, and an aryl group. L may advantageously represent a monovalent radical chosen from the group formed by methyl, ethyl, propyl, 3,3,3-trifluoropropyl, xylyl, tolyl and phenyl. Examples of units of formula (B1) are the following: $H(CH_3)_2SiO_{1/2}$, $H(CH_3)SiO_{2/2}$ and $H(C_6H_5)SiO_{2/2}$.

The organopolysiloxane B may have a linear, branched, cyclic or network structure. When the polyorganosiloxanes are linear polyorganosiloxanes, they essentially consist:
of siloxyl units "D" chosen from the units of formulae $(H)(L)SiO_{2/2}$ and $(L)_2SiO_{2/2}$;
of siloxyl units "M" chosen from the units of formulae $(H)(L)SiO_{1/2}$ and $(L)_3SiO_{2/2}$,
with the symbol L having the same meaning as above and the symbol H denoting a hydrogen atom.

These linear polyorganosiloxanes may be oils having a dynamic viscosity at 25° C. of between 1 mPa·s and 5000 mPa·s, preferentially between 1 mPa·s and 1000 mPa·s, and even more preferentially between 1 mPa·s and 500 mPa·s.

When the polyorganosiloxanes are cyclic polyorganosiloxanes, they may consist of siloxyl units "D" chosen from the units of formulae $HLSiO_{2/2}$ and $L_2SiO_{2/2}$, or of siloxyl units of formula $HLSiO_{2/2}$ only. The units of formula $L_2SiO_{2/2}$ may in particular be dialkylsiloxy units or to alkylarylsiloxy units. These cyclic polyorganosiloxanes can have a dynamic viscosity at 25° C. of between 1 mPa·s and 5 000 mPa·s.

Examples of organopolysiloxane B are:
polydimethylsiloxanes comprising hydrodimethylsilyl end groups;
poly(dimethylsiloxane-co-hydromethylsiloxane)s comprising trimethylsilyl end groups;

poly(dimethylsiloxane-co-hydromethylsiloxane)s comprising hydrodimethylsilyl end groups;
polyhydromethylsiloxanes comprising trimthylsilyl end groups;
cyclic hydromethylpolysiloxanes.

When the polyorganosiloxanes are branched or network polyorganosiloxanes, they can also comprise:
siloxyl units "T" chosen from the units of formulae $(H)(L)SiO_{3/2}$ and $(L)_2SiO_{3/2}$;
siloxyl units "Q" of formula $SiO_{4/2}$,
with the symbol H representing a hydrogen atom and L having the same meaning as above.

According to one particularly advantageous embodiment, the silicone composition X comprise at least two different organopolysiloxanes B which are:
a) a chain extender $B^{ext}$ comprising:
end monovalent siloxy units, which may be identical or different, of formula (M):

$$(H)_p(R^1)_q SiS_{1/2} \quad (M)$$

in which the symbol $R^1$ corresponds to a $C_1$ to $C_8$ alkyl group; the symbol H represents a hydrogen atom and with p=0 or 1, q=2 or 3 and (p+q)=3;
divalent siloxy units, which may be identical or different, of formula (D):

$$(H)_n(R^2)_m SiO_{2/2} \quad (D)$$

in which the radical $R^2$ corresponds to a $C_1$ to $C_8$ alkyl group or an aryl group, the symbol H represents a hydrogen atom and with n=0 or 1, m=1 or 2 and (n+m)=2, and
with the condition according to which the organopolysiloxane $B^{ext}$ comprises two hydrogen atoms each bonded to a different silicon atom per polymer, that is to say two Si—H functions per polymer;
b) a crosslinking agent $B^{ret}$ comprising:
at least three siloxy units of formula (B.1):

$$(H)_e(L)_e SiO_{(3-e)/2} \quad (B.1)$$

in which the symbol H represents a hydrogen atom, the symbol L represents an alkyl having from 1 to 8 carbon atoms inclusive or an aryl such as xylyl, tolyl or phenyl, and the symbol e is equal to 0, 1 or 2; and
optionally other siloxy units of formula (B-2):

$$(L)g SiO(4-g)/2$$

in which the symbol L represents an alkyl having from 1 to 8 carbon atoms inclusive and the symbol g is equal to 0, 1, 2 or 3.

This embodiment using a mixture of organopolysiloxane B acting as chain extender ($B^{ext}$) and of organopolysiloxane acting as crosslinking agent $B^{ret}$ makes it possible to obtain gels having improved adhesion properties, in particular with respect to the support S employed. Those skilled in the art, depending on the type of support used, will know how to vary the weight contents of each organopolysiloxane acting as chain extender ($B^{ext}$) and of organopolysiloxane A acting as crosslinking agent $B^{ret}$. For example, reference may be made to the teaching described in patent application EP-0737721-B1 filed by the company Rhodia Chimie.

Chain extender organopolysiloxanes $B^{ext}$ that are particularly advantageous are the polydimethylsiloxanes comprising dimethylhydrosilyl end groups having a dynamic viscosity at 25° C. of between 1 mPa·s and 500 mPa·s, preferably of between 1 mPa·s and 250 mPa·s, and even more preferentially of between 1 and 50 mPa·s. The formula of these particularly advantageous organopolysiloxanes $B^{ext}$ is $M^H D_x M^H$, in which formula:

$M^H$=siloxy unit of formula: $(H)(CH_3)_2 SiO_{1/2}$

D=siloxyl unit of formula: $(CH_3)_2 SiO_{2/2}$, and x is an integer between 0 and 100, preferably between 1 and 50 and even more preferentially between 3 and 30.

Crosslinking organopolysiloxanes $B^{ret}$ that are particularly advantageous are the polydimethylsiloxanes comprising dimethylhydrosilyl end groups having a dynamic viscosity at 25° C. of between 1 mPa·s and 2000 mPa·s, preferably of between 1 mPa·s and 1000 mPa·s, and even more preferentially of between 1 and 500 mPa·s. The formulae of these particularly advantageous organopolysiloxanes $B^{ret}$ are:

$$M^H D_x D_w^H M^H$$

$$M^H D_x D_y^H M$$

$$M D_x D_z^H M$$

in which formulae:

$M^H$=siloxy unit of formula: $(H)(CH_3)_2 SiO_{1/2}$ $D^H$=siloxy unit of formula: $(H)(CH_3)SiO_{2/2}$ D=siloxyl unit of formula: $(CH_3)_2 SiO_{2/2}$, and M=siloxy unit of formula: $(CH_3)_3 SiO_{1/2}$ with:
x a number between 0 and 500, preferably between 10 and 250 and even more preferentially between 50 and 150;
w an integer between 1 and 500, preferably between 1 and 250 or between 1 and 100 and even more preferentially between 1 and 20;
y an integer between 2 and 500, preferably between 2 and 250 or between 2 and 100 and even more preferentially between 2 and 20; and
z an integer between 3 and 500, preferably between 3 and 250 or between 3 and 100 and even more preferentially between 3 and 20.

According to one preferred embodiment, the choice and the amount of the chain extender organopolysiloxane $B^{elt}$ and of the crosslinking organopolysiloxane $B^{ret}$ is carried out such that the ratio $r_1$ described above is less than or equal to 80%:

$$r_1 = \frac{\text{Number of moles of SiH function of the extender } B^{ext}}{\text{Total number of moles of SiH function (extender } B^{ext} + \text{crosslinking agents } B^{ret})} \times 100$$

The silicone resin Z is a branched organopolysiloxane polymer comprising siloxy units Q ($SiO_{4/2}$), is well known and is commercially available. It is used in diluted form, preferably diluted in a silicone oil which may bear vinyl functions or a mixture of silicone oil and silicone gum (as described in the present statement). In this case, the choice of the silicone oil and/or of the gum will be carried out so as to have a mixture having a dynamic viscosity at 25° C. (of the diluted form) of between 1000 mPa·s and 100 000 mPa·s.

According to another variant, the silicone resin Z is introduced in the form of a mixture of this resin in a silicone gum.

The silicone resin Z that is particularly useful according to the invention is a silicone resin which has at least one siloxy unit Q and which comprises in its structure from 0.1% to 20% by weight of alkenyl group(s). In this resin, the alkenyl groups may be located on siloxyl units M, D or T. These resins can be prepared for example according to the process described in patent U.S. Pat. No. 2,676,182. A certain number of these resins are commercially available, usually in the form of solutions, for example in xylene.

In one preferred embodiment of the invention, the silicone resin Z is chosen from the group consisting of the silicone resins having the following formulae:

MD$^{Vi}$Q wherein the vinyl groups are included in the units D,

MD$^{Vi}$TQ wherein the vinyl groups are included in the units D,

MM$^{Vi}$Q wherein the vinyl groups are included in some of the units M,

MM$^{Vi}$TQ wherein the vinyl groups are included in some of the units M,

MM$^{Vi}$DD$^{Vi}$Q wherein the vinyl units are included in the units M and D, and mixtures thereof, with:

M=siloxyl unit of formula $R_3SiO_{1/2}$

M$^{Vi}$=siloxyl unit of formula $(R_2)(vinyl)SiO_{1/2}$

D=siloxyl unit of formula $R_2SiO_{2/2}$

D$^{Vi}$=siloxyl unit of formula $(R)(vinyl)SiO_{2/2}$

Q=siloxyl unit of formula $SiO_{4/2}$

T=siloxyl unit of formula $RSiO_{3/2}$, and the groups R, which may be identical or different, are monovalent hydrocarbon-based groups chosen from alkyl groups having from 1 to 8 carbon atoms inclusive, such as methyl, ethyl, propyl and 3,3,3-trifluoropropyl groups, and aryl groups such as xylyl, tolyl and phenyl groups. Preferably, the groups R are methyls.

According to another particular embodiment of the invention, the silicone resin Z is added to the composition according to the invention in the form of a mixture in at least one organopolysiloxane oil, for example corresponding to the definition of the organopolysiloxane A described above, or in at least one hydrocarbon-based solvent such as toluene or xylene, or derivatives known as Exxsol® and sold by the company Exxon Mobil.

Preferably, the silicone resin Z having alkenyl groups bonded to silicon atoms is chosen from the group consisting of:
a silicone resin Z$^1$ of formula MD$^{Vi}$Q in which:
M is a siloxy unit of formula $R_3SiO_{1/2}$ in which R is a $C_1$ to $C_8$ alkyl or an aryl group such as xylyl, tolyl or phenyl,
D$^{Vi}$ is a siloxy unit of formula $RR^1SiO_{2/2}$ with R being a $C_1$ to $C_8$ alkyl or an aryl group and $R^1$ being a vinyl group, and
Q is a siloxy unit of formula $SiO_{4/2}$;
a silicone resin Z$^2$ of formula MM$^{Vi}$Q in which:
M is a siloxy unit of formula $R_3SiO_{12}$ in which R is a $C_1$ to $C_8$ alkyl or an aryl group such as xylyl, tolyl or phenyl, M$^{Vi}$ is a siloxy unit of formula $R_2(Vi)SiO_{1/2}$ with Vi being a vinyl group and R being a $C_1$ to $C_8$ alkyl group or an aryl group such as xylyl, tolyl or phenyl, and
Q is a siloxy unit of formula $SiO_{4/2}$, and
mixtures of the silicone resins Z$^1$ and Z$^2$.

As hydrosilylation catalyst C that is useful according to the invention, mention may be made of the compounds of a metal belonging to the group of platinum which is well known to those skilled in the art. The metals of the platinum group are those known as platinoids, a name which groups together, in addition to platinum, ruthenium, rhodium, palladium, osmium and iridium. The compounds of platinum and of rhodium are preferably used. Use may particularly be made of the complexes of platinum and of an organic product described in patents U.S. Pat. Nos. 3,159,601, 3,159,602 and 3,220,972 and European patents EP-A-0 057 459, EP-A-0 188 978 and EP-A-0 190 530, and the complexes of platinum and of vinyl organosiloxanes described in patent U.S. Pat. No. 3,419,593. The catalyst generally preferred is platinum. By way of examples, mention may be made of black platinum, chloroplatinic acid, a chloroplatinic acid modified with an alcohol, a complex of chloroplatinic acid with an olefin, an aldehyde, a vinylsiloxane or an acetylenic alcohol, among others. The Karstedt solution or complex, as described in patent U.S. Pat. No. 3,775,452, chloroplatinic acid hexahydrate or a platinum catalyst comprising carbene ligands is preferred.

As hydrosilylation reaction inhibitor D that is useful according to the invention, mention may be made of the one chosen from α-acetylenic alcohols, α-α'-acetylenic diesters, ene-yne conjugated compounds, α-acetylenic ketones, acrylonitriles, maleates, fumarates and mixtures thereof. These compounds capable of performing the hydrosilylation inhibitor function are well known to those skilled in the art. They can be used alone or as mixtures.

An inhibitor D of α-acetylenic alcohol type can be chosen from the compounds of following formula (D1):

$$(R^1)(R^2)C(OH)—C≡CH \qquad (D1)$$

in which:
the group R$^1$ represents an alkyl group, a cycloalkyl group, a (cycloalkyl)alkyl group, an aryl group or an arylalkyl group,
the group R$^2$ represents a hydrogen atom, an alkyl group, a cycloalkyl group, a (cycloalkyl)alkyl group, an aryl group or an arylalkyl group,
or else R$^1$ and R$^2$ constitute, together with the carbon atom to which they are bonded, a 5-, 6-, 7- or 8-membered aliphatic ring, optionally substituted one or more times.
According to formula (D1):
the term "alkyl" is intended to mean a saturated hydrocarbon-based chain containing from 1 to 20 carbon atoms and preferably from 1 to 8 carbon atoms. An alkyl group may be chosen from the group consisting of methyl, ethyl, isopropyl, n-propyl, tert-butyl, isobutyl, n-butyl, n-pentyl, isoamyl and 1,1-dimethylpropyl groups;
the term "cycloalkyl" is intended to mean according to the invention a saturated monocyclic or polycyclic, preferably monocyclic or bicyclic, hydrocarbon-based group containing from 3 to 20 carbon atoms, preferably from 5 to 8 carbon atoms. When the cycloalkyl group is polycyclic, the multiple cyclic nuclei may be attached to each other via a covalent bond and/or via a spirane atom and/or may be fused with each other. A cycloalkyl group may be chosen from the group consisting of cyclopropyl, cyclobutyl, cyclopentyl, cyclohexyl, cycloheptyl, cyclooctyl, adamantane and norbornane;

the term "(cycloalkyl)alkyl" is intended to mean according to the invention a cycloalkyl group as defined above bonded to an alkyl group also as defined above;

the term "aryl" is intended to mean according to the invention a monocyclic or polycyclic aromatic hydrocarbon-based group containing from 5 to 18 carbon atoms. An aryl group may be chosen from the group consisting of phenyl, naphthyl, anthracenyl and phenanthryl;

the term "arylalkyl" is intended to mean according to the invention an aryl group as defined above bonded to an alkyl group also as defined above.

According to one preferred embodiment, in formula (D1), $R^1$ and $R^2$ constitute, together with the carbon atom to which they are bonded, an unsubstituted 5-, 6-, 7- or 8-membered aliphatic ring. According to another preferred embodiment, $R^1$ and $R^2$, which may be identical or different, represent, independently of one another, a $C_1$ to $C_{12}$, preferably $C_1$ to $C_6$, monovalent alkyl group.

An inhibitor D which is an α-acetylenic alcohol that is useful according to the invention can be chosen from the group consisting of the following compounds: 1-ethynyl-1-cyclopentanol; 1-ethynyl-1-cyclohexanol (also called ECH); 1-ethynyl-1-cycloheptanol; 1-ethynyl-1-cyclooctanol; 3-methyl-1-butyn-3-ol (also called MBT); 3-methyl-1-pentyn-3-ol; 3-methyl-1-hexp-3-ol; 3-methyl-1-heptyn-3-ol; 3-methyl-1-octyn-3-ol; 3-methyl-1-nonyn-3-ol; 3-methyl-1-decyn-3-ol; 3-methyl-1-dodecyn-3-ol; 3-methyl-1-pentadecyn-3-ol; 3-ethyl-1-pentyn-3-ol; 3-ethyl-1-hexp-3-ol; 3-ethyl-1-heptyn-3-ol; 3,5-dimethyl-1-hexp-3-ol; 3-isobutyl-5-methyl-1-hexp-3-ol; 3,4,4-tri methyl-1-pentyn-3-ol; 3-ethyl-5-methyl-1-heptyn-3-ol; 3,6-diethyl-1-nonyn-3-ol; 3,7,11-trimethyl-1-dodecyn-3-ol (also called TMDDO); 1,1-diphenyl-2-propyn-1-ol; 3-butyn-2-ol; 1-pentyn-3-ol; 1-hexp-3-ol; 1-heptyn-3-ol; 5-methyl-1-hexp-3-ol; 4-ethyl-1-octyn-3-ol and 9-ethynyl-9-fluorenol.

An inhibitor D of α, α-acetylenic diester type can be chosen from the compounds of formula (D2) below:

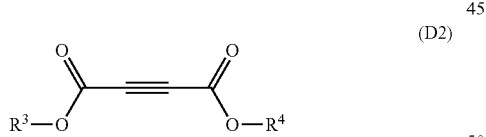

(D2)

in which the groups $R^3$ and $R^4$, which may be identical or different, represent, independently of one another, an alkyl group, a cycloalkyl group, a (cycloalkyl)alkyl group, an aryl group, an arylalkyl group or a silyl group.

The term "silyl" is intended to mean according to the invention a group of formula —$SiR_3$, each R independently representing an alkyl group containing from 1 to 20 carbon atoms, preferably from 1 to 8 carbon atoms. A silyl group can for example be the trimethylsilyl group.

According to one particular embodiment, in formula (D2), $R^3$ and $R^4$, which may be identical or different, independently of one another represent a $C_1$ to $C_{12}$, preferably $C_1$ to $C_6$, alkyl group or the trimethylsilyl group. An inhibitor D which is an α-α'-acetylenic diester that is useful according to the invention can be chosen from the group consisting of the following compounds: dimethyl acetylenedicarboxylate (DMAD), diethyl acetylenedicarboxylate, tert-butyl acetylenedicarboxylate and bis(trimethylsilyl) acetylenedicarboxylate.

An inhibitor D of ene-yne conjugated compound type can be chosen from the compounds of formula (D3) below:

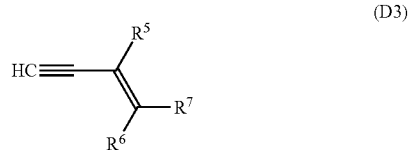

(D3)

in which:

the groups $R^5$, $R^6$ and $R^7$ represent, independently of one another, a hydrogen atom, an alkyl group, a cycloalkyl group, a (cycloalkyl)alkyl group, an aryl group or an arylalkyl group, or else at least two groups among the groups $R^5$, $R_6$ and $R^7$ constitute, together with the carbon atom or atoms to which they are bonded, a 5-, 6-, 7- or 8-membered aliphatic ring, optionally substituted one or more times.

According to one particular embodiment, the groups $R^5$, $R^6$ and $R^7$ represent, independently of one another, a hydrogen atom, a $C_1$ to $C_{12}$, preferably $C_1$ to $C_6$, alkyl group or an aryl group. An inhibitor D which is an ene-yne conjugated compound that is useful according to the invention can be chosen from the group consisting of the following compounds: 3-methyl-3-penten-1-yne; le 3-methyl-3-hexen-1-yne; 2,5-dimethyl-3-hexen-1-yne; le 3-ethyl-3-buten-1-yne; and 3-phenyl-3-buten-1-yne. According to another particular embodiment, two groups chosen from the groups $R^5$, $R^6$ et $R^7$ constitute, together with the carbon atom(s) to which they are bonded, an unsubstituted 5-, 6-, 7- or 8-membered aliphatic ring and the remaining third group represents a hydrogen atom or a $C_1$ to $C_{12}$, preferably $C_1$ to $C_6$, alkyl group. An inhibitor D which is an ene-yne conjugated compound useful according to the invention may be 1-ethynyl-1-cyclohexene.

An inhibitor D of a-acetylenic ketone type can be chosen from the compounds of formula (D4) below:

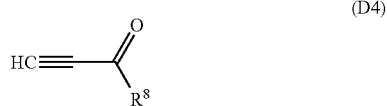

(D4)

in which: $R^8$ represents an alkyl group, a cycloalkyl group, a (cycloalkyl)alkyl group, an aryl group or an arylalkyl group, it being possible for the alkyl, cycloalkyl, (cycloalkyl)alkyl, aryl or arylalkyl groups to optionally be substituted one or more times with a chlorine, bromine or iodine atom.

According to one preferred embodiment, $R^8$ represents a $C_1$ to $C_{12}$, preferably $C_1$ to $C_6$, monovalent alkyl group, optionally substituted one or more times with a chlorine or bromine atom, or a cycloalkyl group, or an aryl group. An inhibitor D which is an a-acetylenic ketone that is useful according to the invention can be chosen from the group consisting of the following compounds: 1-octyn-3-one, 8-chloro-1-octyn-3-one; 8-bromo-1-octyn-3-one; 4,4-dimethyl-1-octyn-3-one; 7-chloro-1-heptyn-3-one; 1-hexyn-3-one; 1-pentyn-3-one; 4-methyl-1-pentyn-3-one; 4,4-dimethyl-1-pentyn-3-one; 1-cyclohexyl-1-propyn-3-one; benzoacetylene and o-chlorobenzoylacetylene.

An inhibitor D of acrylonitrile type can be chosen from the compounds of formula (D5) below:

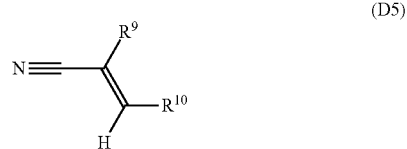

in which: $R^9$ and $R^{19}$ epresent, independently of one another, a hydrogen atom, a chlorine, bromine or iodine atom, an alkyl group, a cycloalkyl group, a (cycloalkyl) alkyl group, an aryl group or an arylalkyl group, it being possible for the alkyl, cycloalkyl, (cycloalkyl) alkyl, aryl or arylalkyl groups to optionally be substituted one or more times with a chlorine, bromine or iodine atom.

An inhibitor D which is an acrylonitrile that is useful according to the invention can be chosen from the group consisting of the following compounds: acrylonitrile; methacrylonitrile; 2-chloroacrylonitrile; crotonitrile and cinnamonitrile.

An inhibitor D of maleate or fumarate type can be chosen from the compounds of formulae (D6) and (D7) below:

in which: $R^{11}$ and $R^{12}$, which may be identical or different, represent, independently of one another, an alkyl or alkenyl group, a cycloalkyl group, a (cycloalkyl)alkyl group, an aryl group or an arylalkyl group, said alkyl, alkenyl, cycloalkyl, (cycloalkyl)alkyl, aryl and arylalkyl groups possibly being substituted with an alkoxy group. The term "alkenyl" is intended to mean according to the invention a saturated hydrocarbon-based chain containing from 1 to 20 carbon atoms, preferably from 1 to 6 carbon atoms, and comprising at least one double unsaturation. Preferably, the alkenyl group is chosen from the group consisting of a vinyl or an allyl.

The term "alkoxy" is intended to mean, according to formula (D6) or (D7), an alkyl group as defined above bonded to an oxygen atom. An alkoxy group can be chosen from the group consisting of methoxy, ethoxy, proproxy and butoxy.

According to one particular embodiment, $R^{11}$ and $R^{12}$, which may be identical or different, represent, independently of one another, a $C_1$ to $C_{12}$, preferably $C_1$ to $C_6$, alkyl or alkenyl group optionally substituted with a $C_1$ to $C_6$ alkoxy group.

An inhibitor D which is a maleate or a fumarate that is useful according to the invention can be chosen from the group consisting of diethyl fumarate, diethyl maleate, diallyl fumarate, diallyl maleate and bis(methoxyisopropyl) maleate.

Inhibitors D chosen from a-acetylenic alcohols, α-α'-acetylenic diesters, ene-yne conjugated compounds, a-acetylenic ketones, acrylonitriles, maleates and fumarates are commercially available. Mention may in particular be made of ECH (1-ethynyl-1-cyclohexanol) which is commercially available from BASF, dimethyl maleate which is commercially available from DMS and dimethyl acetylenedicarboxylate which is commercially available from City Chemical LLC.

These inhibitors are added in a weight amount of between 1 and 50 000 ppm relative to the weight of the total silicone composition, in particular between 10 and 10 000 ppm, preferably between 20 and 2000 ppm and even more preferentially between 20 ppm and 500 ppm.

As an example of a stabilizing additive K, mention may for example be made of silylated derivatives of phosphoric acid, such as phosphoric acid silyl esters.

Particularly advantageous results are obtained when the silicone composition X comprises:

1) at least one organopolysiloxane A which is a polydimethylsiloxane comprising dimethylvinylsilyl end groups having a dynamic viscosity at 25° C. of between 50 mPa·s and 120 000 mPa·s, and preferably of between 100 mPa·s and 80 000 mPa·s and having a formula $M^{Vi}D_xM^{Vi}$, in which formula:

$M^{Vi}$=siloxy unit of formula: (vinyl)(CH$_3$)$_2$SiO$_{1/2}$

D=siloxyl unit of formula: (CH$_3$)$_2$SiO$_{2/2}$, and x is a number between 0 and 1000, and preferably between 5 and 1000, 2) a chain extender organopolysiloxane $B^{ext}$ of formula $M^HD_xM^H$ with:

$M^H$=siloxy unit of formula: (H)(CH$_3$)$_2$SiO$_{1/2}$

D=siloxy unit of formula: (CH$_3$)$_2$SiO$_{2/2}$, and x being a number between 3 and 30, 3) a crosslinking organopolysiloxane $B^{ret}$ of formula $M^HD_x D_w{}^HM^H$ or $M^HD_xD_yH^M$, in which formulae:

$M^H$=siloxy unit of formula: (H)(CH$_3$)$_2$SiO$_{1/2}$

M=siloxy unit of formula: (CH$_3$)$_3$SiO$_{1/2}$

D=siloxy unit of formula: (CH$_3$)$_2$SiO$_{2/2}$, and $D^H$=siloxy unit of formula: (CH$_3$)(H)SiO$_{2/2}$, and x is a number between 50 and 150,
w is a number between 1 and 20, and
y is a number between 2 and 20, 4) at least one hydrosilylation catalyst C,
5) at least one hydrosilylation reaction inhibitor D,
6) optionally at least one additive K, and
7) between 1.5% and 3.5% by weight, and preferably between 1.75% and 3.0% by weight, relative to the total weight of the silicone composition X, of at least one silicone resin $Z^1$ of formula MD$^{Vi}$Q and as described above and/or at least one silicone resin $Z^2$ of formula MM$^{Vi}$Q and as described above, and with the following conditions:

a) the amounts by weight of the organopolysiloxanes A, B, $Z^1$ and $Z^2$ are determined such that the value of the ratio $RH_{alk}=n_H/t_{Alk}$ is included in the following range: $0.10 \leq RH_{alk} \leq 0.80$, preferably in the following range $0.20 \leq RH_{alk} \leq 0.80$, and even more preferentially in the following range $0.20 \leq RH_{alk} \leq 0.75$, with $n_H$=number of moles of hydrogen atom directly bonded to a silicon atom of the organopolysiloxanes $B^{ext}$ and $B^{ret}$ and $t_{Alk}$=number of moles of alkenyl directly bonded to a silicon atom of the organopolysiloxane A and of the silicone resin $Z^1$ or $Z^2$ or of the mixture of resins $Z^1$ and $Z^2$, and b) the viscosities and the amounts by weight of the constituents of the silicone composition X are chosen such that the dynamic viscosity at 25° C. of the silicone composition X is between 200 mPa·s and 100 000 mPa·s, and preferably between 200 mPa·s and 80 000 mPa·s.

According to one particularly advantageous embodiment, the silicone composition X comprises, as organopolysiloxane A, at least two organopolysiloxanes A1 and A2 comprising, per molecule, at least two $C_2$ to $C_6$ alkenyl radicals each bonded to a silicon atom, characterized in that:
a) the organopolysiloxane A1 has a dynamic viscosity at 25° C. of between 100 mPa·s and 120 000 mPa·s, and
b) the organopolysiloxane A2 is a gum having a consistency at 25° C. of between 500 mm/10 and 1000 mm/10.

Preferably, the two organopolysiloxanes A1 and A2 are polydimethylsiloxanes comprising dimethylvinylsilyl end groups and characterized in that:
a) the organopolysiloxane A1 has a dynamic viscosity at 25° C. of between 100 mPa·s and 120 000 mPa·s, and
b) the organopolysiloxane A2 is a gum having a consistency at 25° C. of between 500 mm/10 and 1000 mm/10.

The term "gum" is used for organosiliceous compounds having viscosities conventionally greater than ~600 000 mPa·s, which corresponds to a molecular weight of greater than 260 000 g/mol. The consistency of a gum is determined at 25° C. by means of a penetrometer of PNR12 type or equivalent model which makes it possible to apply a cylindrical head, under standardized conditions, to the sample. The consistency of a gum is the depth, expressed in tenths of millimetres, to which a calibrated cylinder penetrates into the sample over the course of one minute. To this effect, a sample of gum is introduced into an aluminum bucket 40 mm in diameter and 60 mm in height. The bronze or brass cylindrical head measures 6.35 mm in diameter and 4.76 mm in height and is carried by a metal rod 51 mm long and 3 mm in diameter, which is suitable for the penetrometer. This rod is ballasted with an overload of 100 g. The total weight of the assembly is 151.8 g. The bucket containing the sample of gum is placed in the bath thermostated at 25° C.±0.5° for a minimum of 30 minutes. The measurement is carried out according to the constructor's instructions.

According to one preferred variant, the silicone composition X comprises at least three organopolysiloxanes A as described above and comprising, per molecule, at least two $C_2$ to $C_6$ alkenyl radicals each bonded to a silicon atom:
a) the first having a viscosity of between 100 mPa·s and 5000 mPa·s,
b) the second having a viscosity of between 5000 mPa·s and 15 000 mPa·s, and
c) the third having a viscosity of between 15 000 mPa·s and 100 000 mPa·s.

The last subject according to the invention relates to an item that adheres to the skin, characterized in that it is a medical device or an element of a medical device.

As examples of medical devices, mention may be made of a dressing that adheres to the skin, in particular intended for non-traumatic removal from healthy skin and from a wound, or a device for holding in place medical accessories used in contact with the skin, of sensor, probe, catheter or needle type.

The nonlimiting examples which follow show various possibilities of formulation of the compositions according to the invention and also the characteristics and the properties of the silicone gels obtained by crosslinking said compositions.

EXAMPLES

1) Measurement of the Tack:

The test is carried out according to the standard ASTM D2979 with a PROBE TACK device (PT-1000). A cylindrical punch with a flat face is brought into contact with the gel of the composite to be tested (surface area of contact with the gel=0.2 cm²). The composite consists of a PET support (thickness of 36 μm) coated with 200 g/m² of the precursor silicone composition for the gel. The punch is then kept in contact with the gel for a contact time of 1 second at a constant pressure of 100 gf/cm². Next, the punch is detached from the gel at a constant speed of 10 mm/s, and the force required to separate the gel from the rod is measured and expressed in gf/cm².

2) The adhesive power at 180° or peel test at 180°

The composite consists of a PET support (thickness of 36 μm) coated with 200 g/m² of the precursor silicone composition for the gel. The adhesive power at 180° is evaluated by the method described in the document FINAT Test Method n° 1 (FINAT Technical Handbook 6th Edition, 2001). Thus, the silicone gel of the composite to be tested (dimensions=15 cm in length and 4 cm in width) is brought into contact with a sheet of Bristol paper (brand-name Exacompta®). The composite is then detached with an angle of 180° with a constant speed of 300 mm/min and with the aid of a 10 N force cell. The force is measured and related to the width of the item and expressed in N/cm.

3) Static Shear Strength

The composite consists of a PET support (thickness of 36 μm) coated with 200 g/m² of the precursor silicone composition for the gel.

The static shear strength is evaluated by means of the method described in the document "FINAT Test Method no. 8" (FINAT Technical Handbook 6th Edition, 2001).

The composite (dimensions: 4.5 cm×2.5 cm) is adhesively bonded to a metal (stainless steel) plate and is subjected to a weight of 1 kg. The time required until the weight drops is measured in hours and corresponds to the shear.

4) Calculation of the Ratio $r_1$ $$r_1 = \frac{\text{Number of moles of SiH function of the extruder } B^{ext}}{\text{Total number of moles of SiH function (extruder } B^{ext} + \text{crosslinking agent } B^{ret})} \times 100$$

5) Preparation of the Gel Precursor Silicone Compositions According to the Invention
   a) Starting Materials Used
   POS A1=α,ω-(dimethylvinylsiloxy) polydimethylsiloxane oil having a dynamic viscosity at 25° C. equal to 60 000 mPa·s.

POS A2=α,ω-(dimethylvinylsiloxy) polydimethylsiloxane oil having a dynamic viscosity at 25° C. equal to 10000 mPa·s.

POS A3=α,ω-(dimethylvinylsiloxy) polydimethylsiloxane oil having a dynamic viscosity at 25° C. equal to 3500 mPa·s.

Silicone resin $Z^1$: of formula $MD^{Vi}Q$ in which:
  M is a siloxy unit of formula: $(CH_3)_3SiO_{1/2}$
  $D^{Vi}$ is a siloxy unit of formula $(CH_3)(vinyl)SiO_{2/2}$
  Q is a siloxy unit of formula $SiO_{4/2}$ Silicone resin $Z^2$ of formula $MM^{Vi}Q$ in which:
  M is a siloxy unit of formula $(CH_3)_3SiO_{1/2}$
  $M^{Vi}$ is a siloxy unit of formula: $(CH_3)_2(vinyl)SiO_{1/2}$; and
  Q is a siloxy unit of formula $SiO_{4/2}$, EXT=POS $B1^{ext}$: poly(dimethylsiloxy)-α, ω-dimethylhydrosiloxy oil having a viscosity of approximately 8.5 mPa·s and containing on average 5.7% by weight of SiH unit; structure of the type:
  $M^HD_xM^H$ with x between on average 7 and 15;

XL=POS $B1^{ret}$: poly(dimethylsiloxy) (methylhydrosiloxy) α, ω-dimethylhydrosiloxy oil having an average viscosity of 70 mPa·s and containing approximately 1.9% by weight of SiH group; structure of the type:
  $M^HD_xD_w{}^HM^H$ with x between on average 70 and 80 and w on average between 1 and 3;

Cata. (C)=platinum organometallic catalyst used as reaction catalyst.

ECH=hydrosilylation reaction inhibitor=1-ethynyl-1-cyclohexanol

Stabilizer K=phosphoric acid silyl ester.

b) Preparation of the Composites (=Support Coated with a Silicone Gel)

The silicone compositions tested are in the two-component form. The parts called Part A and Part B are then mixed in a 1:1 weight ratio. The precursor silicone composition for a gel is then applied, at a weight of 200 g/m², to a PET support (thickness of 36 μm) using a coating scraper. After the coating, the crosslinking of the composite is carried out for 30 min at 120° C. in a ventilated oven so as to obtain a support coated with a gel.

For composite n° 1, a gel is used which is obtained from the precursor silicone composition for the gel and sold under the name Gel silicone Silbione® HC2 2022 by the company Bluestar Silicones.

For composite n° 2, a gel is used which is obtained from the following silicone composition (mixture of parts A and B, weight ratio 1:1)

TABLE 1

Composition of the gel for composite n° 2

| PART A | | PART B | |
|---|---|---|---|
| Constituents | % by weight | Constituents | % by weight |
| POS A1 | 2.989 | POS A1 | 26.65 |
| POS A2 | 97.000 | POS A2 | 55.90 |
| Cata. (C) | 0.066 | ECH | 0.012 |
| | | Silicone resin $Z^1$ | 2.50 |
| | | POS A3 | 7.50 |
| | | Stabilizer K | 0.04 |
| | | XL | 5.70 |
| | | EXT | 1.74 |

Formulation n° 2: $RH_{alk}$=0.62, weight of silicone resin $Z^1$=1.25% by weight relative to the total weight of the composition and r1=45%, viscosity after mixing of parts A and B=12 000 mPa·s For composite n° 3, a gel is used which is obtained from the following silicone composition (mixture of parts A and B, weight ratio 1:1)

TABLE 2

Composition of the gel for composite n° 3

| PART A | | PART B | |
|---|---|---|---|
| Constituents | % by weight | Constituents | % by weight |
| POS A1 | 2.989 | POS A1 | 21.96 |
| POS A2 | 97.000 | POS A2 | 49.49 |
| Cata. (C) | 0.066 | ECH | 0.012 |
| | | Silicone resin $Z^1$ | 5.00 |
| | | POS A3 | 15.00 |
| | | Stabilizer K | 0.04 |
| | | XL | 6.60 |
| | | EXT | 2.01 |

Formulation n° 3: $RH_{alk}$=0.62, weight of silicone resin $Z^1$=2.50% by weight relative to the total weight of the composition and r1=45%, viscosity after mixing of parts A and B=10 000 mPa·s For composite n° 4, a gel is used which is obtained from the following silicone composition (mixture of parts A and B, weight ratio 1:1)

TABLE 3

Composition of the gel for composite n° 4

| PART A | | PART B | |
|---|---|---|---|
| Constituents | % by weight | Constituents | % by weight |
| POS A1 | 2.989 | POS A1 | 25.29 |
| POS A2 | 97.000 | POS A2 | 56.08 |
| Cata. (C) | 0.011 | ECH | 0.012 |
| | | Silicone resin $Z^2$ | 4.00 |
| | | POS A3 | 2.00 |
| | | POS A1 | 4.00 |
| | | Stabilizer K | 0.04 |
| | | XL | 6.60 |
| | | EXT | 2.00 |

Formulation n° 4: $RH_{alk}$=0.62, weight of silicone resin $Z^2$=2% by weight relative to the total weight of the composition and r1=45%, viscosity after mixing of parts A and B=15 000 mPa·s For composite n° 5, a gel is used which is obtained from the following silicone composition (mixture of parts A and B, weight ratio 1:1)

TABLE 4

Composition of the gel for composite n° 5

| PART A | | PART B | |
|---|---|---|---|
| Constituents | % by weight | Constituents | % by weight |
| POS A1 | 2.989 | POS A1 | 21.29 |
| POS A2 | 97.000 | POS A2 | 47.77 |
| Cata. (C) | 0.011 | ECH | 0.012 |
| | | Silicone resin $Z^2$ | 8.00 |
| | | POS A3 | 4.00 |
| | | POS A1 | 8.00 |
| | | Stabilizer K | 0.04 |
| | | XL | 8.38 |
| | | EXT | 2.55 |

Formulation n° 5: $RH_{alk}$=0.62, weight of silicone resin $Z^2$=4% by weight relative to the total weight of the composition and r1=45%, viscosity after mixing of parts A and B=15 000 mPa·s

TABLE 5

Properties of the composites tested

| Composites (supports coated with silicone gel) | Silicone resin tested | Amount in the silicone composition (%) | Penetration (mm/10) | Peel 200 g/m$^2$ (N/cm) | Tack (gf/cm$^2$) | Shear (hours) |
|---|---|---|---|---|---|---|
| no1 Comparative | | 0 | 155 | 1.03 | 600 | <1 |
| no2 Comparative | silicone resin Z$^1$ | 1.25 | 154 | 1.19 | 758 | 3 |
| no3 Invention | | 2.50 | 132 | 1.16 | 832 | 11 |
| no4 Invention | silicone resin Z$^2$ | 2.00 | 118 | 1.14 | 780 | 16 |
| no5 Comparative | | 4.00 | Not measured | 0.3 | 292 | 13.7 |

The introduction of the resin Z$^1$ at 2.50% by weight, relative to the total weight of the composition, or of the resin Z$^2$ at 2% by weight, relative to the total weight of the composition, makes it possible to achieve optimal performances (all the properties are improved compared with the comparative composite n° 1 and in particular the shear strength) while at the same time retaining the optimal tack properties.

The invention claimed is:

1. An item that adheres to the skin, the item comprising:
   a support S having a top face S1 and a bottom face S2,
   optionally at least one tie primer C1 applied on at least one part or on all of the top face S1 of the support S,
   at least one layer D1 applied continuously or discontinuously on the top face S1 of the support S or on the tie primer C1 when it is present, and which comprises a silicone gel E that adheres to the skin, the silicone gel E having the following properties:
   a) a penetrability of from 80 mm/10 to 300 mm/10, measured according to the standard NF ISO 2137 with a penetrometer having a rod and a cone and the sum of the weights of which is equal to 62.5 g, and
   b) a tack of from 600 gf/cm$^2$ to 900 gf/cm$^2$, for a layer of 200 g/m$^2$ coated onto a PET support having a thickness of 36 μm and measured according to the standard ASTM D2979,
   c) an adhesive power of from 1.05 N/cm to 1.25 N/cm, for a layer of 200 g/m$^2$ coated onto a PET support having a thickness of 36 μm and measured according to the FINAT no. 1 test method by bringing into contact with a strip of Bristol paper into contact with a peel angle of 180°, and
   d) a static shear strength at 23° C. greater than 3 hours measured according to the FINAT no. 8 test method for a layer of 200 g/m$^2$ coated onto a PET support having a thickness of 36 μm; and
   optionally at least one protective layer F comprising a peel-off protective material and applied on the layer D1,
   the silicone gel E being obtained by crosslinking of a silicone composition X comprising:
1) at least one organopolysiloxane A comprising, per molecule, at least two C$_2$-C$_6$ alkenyl radicals each bonded to a silicon atom and consisting of:
   (i) at least two units of formula (A1):

$$(Y)_a(Z)_b SiO_{(4-(a+b))/2} \quad (A1)$$

in which:
   Y represents a C$_2$ to C$_6$ alkenyl group,
   Z represents a monovalent hydrocarbon-based group chosen from alkyl groups having from 1 to 8 carbon atoms inclusive, cycloalkyl groups, and aryl groups;
   a and b represent integers, a being 1, 2 or 3, b being 0, 1 or 2 and (a+b) being 2 or 3;
   (ii) and optionally at least one unit of formula (A2):

$$(Z)_c SiO_{(4-c)/2} \quad (A2)$$

in which:
   Z has the same meaning as above, and
   c represents an integer which is 2 or 3,
2) at least one organopolysiloxane B comprising, per molecule, at least two hydrogen atoms each bonded to a silicon atom,
3) at least one hydrosilylation catalyst C,
4) at least one hydrosilylation reaction inhibitor D,
5) optionally at least one additive K, and
6) from 1.5% to 3.5% by weight, relative to the total weight of the silicone composition X, of at least one silicone resin Z having alkenyl groups bonded to silicon atoms and comprising:
   a) at least one siloxyl unit of formula (I):

$$YR_a SiO_{\frac{(3-a)}{2}} \quad (I)$$

in which:
   Y represents a C$_2$ to C$_6$ alkenyl group,
   R is a monovalent hydrocarbon-based group chosen from alkyl groups having from 1 to 8 carbon atoms inclusive, cycloalkyl groups, and aryl groups, and
   a=0, 1 or 2,
   b) at least one siloxy unit of formula (II):

$$R_b SiO_{\frac{(4-b)}{2}} \quad (II)$$

in which R has the same definition as above and b=1, 2 or 3; and
   c) at least one siloxy unit Q of formula (III):

$$SiO_{\frac{4}{2}} \quad (III)$$

with the following conditions:
a) the value of the ratio $RH_{alk}=n_H/t_{Alk}$ is included in the following range: $0.10 \leq RH_{alk} \leq 0.80$, with $n_H$=number of moles of hydrogen atom directly bonded to a silicon atom of the organopolysiloxane B and $t_{Alk}$=number of moles of alkenyl directly bonded to a silicon atom of the organopolysiloxane A and of the silicone resin Z, and
b) the dynamic viscosity of the silicone composition X is from 200 mPa·s to 100 000 mPa·s at 25° C.

2. The item as claimed in claim 1, comprising the at least one tie primer C1.

3. The item as claimed in claim 1, wherein the silicone resin Z is selected from the group consisting of:
a silicone resin $Z^1$ of formula $MD^{Vi}Q$ in which:
M is a siloxy unit of formula $R_3SiO_{1/2}$ in which R is a $C_1$ to $C_8$ alkyl or an aryl group,
$D^{Vi}$ is a siloxy unit of formula $RR^1SiO_{2/2}$ with R being a $C_1$ to $C_8$ alkyl or an aryl group and $R^1$ being a vinyl group, and
Q is a siloxy unit of formula $SiO_{4/2}$;
a silicone resin $Z^2$ of formula $MM^{Vi}Q$ in which:
M is a siloxy unit of formula $R_3SiO_{1/2}$ in which R is a $C_1$ to $C_8$ alkyl or an aryl group,
$M^{Vi}$ is a siloxy unit of formula $R_2(Vi)SiO_{1/2}$ with Vi being a vinyl group and R being a $C_1$ to $C_8$ alkyl group or an aryl group, and
Q is a siloxy unit of formula $SiO_{4/2}$, and
mixtures of the silicone resins $Z^1$ and $Z^2$.

4. The item as claimed in claim 1, wherein the silicone composition X comprises at least two different organopolysiloxanes B which are:
a) a chain extender $B^{ert}$ comprising:
end monovalent siloxy units, which are identical or different, of formula (M):

(H)$_p$(R$^1$)$_q$SiO$_{1/2}$ (M)

in which the symbol $R^1$ corresponds to a $C_1$ to $C_8$ alkyl group; the symbol H represents a hydrogen atom and with p=0 or 1, q=2 or 3 and (p+q)=3;
divalent siloxy units, which are identical or different, of formula (D):

(H)$_n$(R$^2$)$_m$SiO$_{2/2}$ (D)

in which the radical $R^2$ corresponds to a $C_1$ to $C_8$ alkyl group or an aryl group, the symbol H represents a hydrogen atom and with n=0 or 1, m=1 or 2 and (n+m)=2, and
with the condition according to which the chain extender $B^{ext}$ comprises, per molecule, two hydrogen atoms each bonded to a different silicon atom, that is to say two Si—H functions per molecule;
b) a crosslinking agent $B^{ret}$ comprising:
at least three siloxy units of formula (B.1):

(H)(L)$_e$SiO$_{(3-e)/2}$ (B.1)

in which the symbol H represents a hydrogen atom, the symbol L represents an alkyl having from 1 to 8 carbon atoms inclusive or an aryl, and the symbol e is equal to 0, 1 or 2; and
optionally other siloxy units of formula (B-2):

(L)$_g$SiO$_{(4-g)/2}$ in which the symbol L represents an alkyl having from 1 to 8 carbon atoms inclusive and the symbol g is equal to 0, 1, 2 or 3.

5. The item as claimed in claim 1, wherein the at least one organopolysiloxane A comprises at least two organopolysiloxanes A1 and A2 comprising, per molecule, at least two $C_2$ to $C_6$ alkenyl radicals each bonded to a silicon atom, wherein:
a) the organopolysiloxane A1 has a dynamic viscosity at 25° C. of from 100 mPa·s to 120 000 mPa·s, and
b) the organopolysiloxane A2 is a gum having a consistency at 25° C. of from 500 mm/10 to 1000 mm/10.

6. The item as claimed in claim 1, wherein the silicone composition X comprises at least three organopolysiloxanes A comprising, per molecule, at least two $C_2$ to $C_6$ alkenyl radicals each bonded to a silicon atom:
a) the first having a dynamic viscosity of from 100 mPa·s to 5000 mPa·s,
b) the second having a dynamic viscosity of from 5000 mPa·s to 15 000 mPa·s, and
c) the third having a dynamic viscosity of from 15 000 mPa·s to 100 000 mPa·s.

7. The item as claimed in claim 1, wherein the support S is composed of a nonwoven material, of a knitted or woven textile material, or of a plastic film.

8. The item as claimed in claim 1, wherein the support S is a perforated flexible polyurethane film or a continuous flexible polyurethane film.

9. The item as claimed in claim 1, comprising one or more layers N comprising an absorbent substance O, optionally separated by one or more intermediate layers P, placed on the support S on the side of the bottom face S2 of the support S.

10. The item as claimed in claim 1, wherein the support S is a flexible polyurethane film and comprises, on at least one part of the bottom face S2, a pressure-sensitive adhesive.

11. The item as claimed in claim 1, wherein it is a dressing, a part of a dressing, or a part of a medical device for holding a sensor, probe, catheter, needle or ostomy bag in contact with the skin.

12. The item as claimed in claim 1, wherein the penetrability of the silicone gel E is from 80 mm/10 to 200 mm/10.

13. The item as claimed in claim 1, wherein the tack of the silicone gel E is from 700 gf/cm$^2$ to 850 gf/cm$^2$.

14. The item as claimed in claim 1, wherein the adhesive power of the silicone gel E is from 1.10 N/cm to 1.20 N/cm.

15. The item as claimed in claim 1, wherein the Y in formula (A1) is a vinyl group.

16. The item as claimed in claim 1, wherein when the Z is an alkyl group having 1 to 8 carbons, Z is a methyl, ethyl, propyl or 3,3,3-trifluoropropyl group.

17. The item as claimed in claim 1, wherein when the Z is a cycloalkyl group, Z is a cyclohexyl, cycloheptyl or cyclooctyl group.

18. The item as claimed in claim 1, wherein when the Z is an aryl group, Z is a xylyl, tolyl or phenyl group.

19. The item as claimed in claim 1, wherein the at least one polyorganosiloxane B comprises at least three hydrogen atoms each bonded to a silicon atom.

20. The item as claimed in claim 1, wherein the silicone composition X comprises 1.75% to 3.0% by weight of at least one silicone resin Z.

21. The item as claimed in claim 1, wherein the Y in formula (I) is a vinyl group.

22. The item as claimed in claim 1, wherein when the R is an alkyl group having 1 to 8 carbon atoms, R is a methyl, ethyl, propyl or 3,3,3-trifluoropropyl group.

23. The item as claimed in claim 1, wherein when the R is a cycloalkyl group, R is a cyclohexyl, cycloheptyl or cyclooctyl group.

24. The item as claimed in claim 1, wherein when the R is an aryl group, R is a xylyl, tolyl or phenyl group.

25. The item as claimed in claim 1, wherein in formula I a=1 or 2.

26. The item as claimed in claim 1, wherein the value of the ratio $RH_{alk}=n_H/t_{Alk}$ is included in the range $0.20 \leq RH_{alk} \leq 0.80$.

27. The item as claimed in claim 1, wherein the value of the ratio $RH_{alk}=n_H/t_{Alk}$ is included in the range range $0.20 \leq RH_{alk} \leq 0.75$.

28. The item as claimed in claim 1, wherein the dynamic viscosity of the silicone composition X is from 200 mPa·s to 80,000 mPa·s at 25° C.

29. The item as claimed in claim 2, wherein the penetrability of the silicone gel E is from 80 mm/10 and 200 mm/10.

30. The item as claimed in claim 2, wherein the tack of the silicone gel E is from 700 gf/cm$^2$ to 850 gf/cm$^2$.

31. The item as claimed in claim 2, wherein the adhesive power of the silicone gel E is from 1.10 N/cm to 1.20 N/cm.

32. The item as claimed in claim 2, wherein the Y in formula (A1) is a vinyl group.

33. The item as claimed in claim 2, wherein when the Z is an alkyl group having 1 to 8 carbons, Z is a methyl, ethyl, propyl or 3,3,3-trifluoropropyl group.

34. The item as claimed in claim 2, wherein when the Z is a cycloalkyl group, Z is a cyclohexyl, cycloheptyl or cyclooctyl group.

35. The item as claimed in claim 2, wherein when the Z is an aryl group, Z is a xylyl, tolyl or phenyl group.

36. The item as claimed in claim 2, wherein the at least one polyorganosiloxane B comprises at least three hydrogen atoms each bonded to a silicon atom.

37. The item as claimed in claim 2, wherein the silicone composition X comprises 1.75% to 3.0% by weight of at least one silicone resin Z.

38. The item as claimed in claim 2, wherein the Y in formula (I) is a vinyl group.

39. The item as claimed in claim 2, wherein when the R is an alkyl group having 1 to 8 carbon atoms, R is a methyl, ethyl, propyl or 3,3,3-trifluoropropyl group.

40. The item as claimed in claim 2, wherein when the R is a cycloalkyl group, R is a cyclohexyl, cycloheptyl or cyclooctyl group.

41. The item as claimed in claim 2, wherein when the R is an aryl group, R is a xylyl, tolyl or phenyl group.

42. The item as claimed in claim 2, wherein in formula (I), a=1 or 2.

43. The item as claimed in claim 2, wherein the value of the ratio $RH_{alk}=n_H/t_{Alk}$ is included in the range $0.20 \leq RH_{alk} \leq 0.80$.

44. The item as claimed in claim 2, wherein the value of the ratio $RH_{alk}=n_H/t_{Alk}$ is included in the range $0.20 \leq RH_{alk} \leq 0.75$.

45. The item as claimed in claim 2, wherein the dynamic viscosity of the silicone composition X is from 200 mPa·s to 80,000 mPa·s at 25° C.

46. The item as claimed in claim 3, wherein the R in the M of the resin $Z^1$ is a xylyl, tolyl or phenyl group.

47. The item as claimed in claim 3, wherein the R in the M of the resin $Z^2$ is a xylyl, tolyl or phenyl group.

48. The item as claimed in claim 3, wherein the R in the $M^{Vi}$ of the resin $Z^2$ is a xylyl, tolyl or phenyl group.

49. The item as claimed in claim 4, wherein the L in formula (B.1) is a xylyl, tolyl or phenyl group.

* * * * *